United States Patent [19]
Okorodudu

[11] 3,980,573
[45] Sept. 14, 1976

[54] SUBSTITUTED DIMERCAPTO THIADIAZOLES AND LUBRICANT COMPOSITIONS CONTAINING SAME

[75] Inventor: Abraham O. M. Okorodudu, West Deptford, N.J.

[73] Assignee: Mobil Oil Corporation, New York, N.Y.

[22] Filed: July 24, 1975

[21] Appl. No.: 598,953

[52] U.S. Cl.............................. 252/46.7; 252/389 A
[51] Int. Cl.$^2$..................... C10M 1/48; C10M 3/42; C10M 5/24; C10M 7/46
[58] Field of Search...................... 252/46.7, 389 A

[56] References Cited
UNITED STATES PATENTS

| | | | |
|---|---|---|---|
| 2,719,125 | 9/1955 | Roberts | 252/46.7 |
| 2,905,639 | 9/1959 | Krzikalla et al. | 252/46.7 |
| 3,361,671 | 1/1968 | Lowe | 252/46.7 |
| 3,816,311 | 6/1974 | Malec | 252/46.7 |
| 3,929,652 | 12/1975 | Seni et al. | 252/46.7 |

*Primary Examiner*—Delbert E. Gantz
*Assistant Examiner*—I. Vaughn
*Attorney, Agent, or Firm*—Charles A. Huggett; Raymond W. Barclay; Claude E. Setliff

[57] ABSTRACT

Lubricants are stabilized against wear and corrosion by adding an additive amount of a novel substituted thiadiazole. These are derived from 2,5-dimercapto-1,3,4-thiadiazole and other moieties, as for example an organophosphorus moiety.

7 Claims, No Drawings

SUBSTITUTED DIMERCAPTO THIADIAZOLES AND LUBRICANT COMPOSITIONS CONTAINING SAME

BACKGROUND OF THE INVENTION

1. Field of the Invention

The invention is concerned with new thiadiazole derivatives and their use as lubricant additives. More particularly the new thiadiazoles are derived from 2,5-dimercapto-1,3,4-thiadiazole and certain other moieties, such as the organophosphorus moiety.

2. Description of the Prior Art

Lubricants are prone to oxidative deterioration when subjected to elevated temperatures or even when they are exposed to atmospheric conditions for long periods of time. Such deterioration of lubricants, including lubricating oils and greases, produces sludge and gums, causes metal parts to corrode and produces loss of lubricating properties of the oil. Many prior art additives are only marginally effective except at unacceptably high concentrations, especially when the lubricants are subjected to drastic oxidizing conditions.

Sulfur containing compounds are widely used as EP additives in lubricants for gear oils and the like. However, they have the disadvantage of tending to corrode metal parts, especially bearings which may contain copper, silver or other sulfur-reactive metals. Consequently, the amount of such additives that can be used is a compromise between maximum EP effectiveness and minimum corrosivity. This problem of balance often becomes quite serious.

It is known that such compounds as

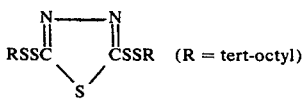

effectively inhibit the corrosion of silver and copper by active sulfur compounds. However, the parent 2,5-dimercapto-1,3,4-thiadiazole lacks solubility in lubricants and for that reason has limited applicability as an anticorrosion agent.

The herein disclosed derivatives of 2,5-dimercapto-1,3,4-thiadiazole are not only lubricant-soluble, but they also exhibit good multifunctionality in that they are excellent anticorrosion agents and impart load carrying properties to the lubricant.

SUMMARY OF THE INVENTION

The invention provides a compound selected from one of the formulas:

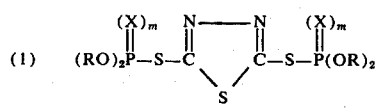

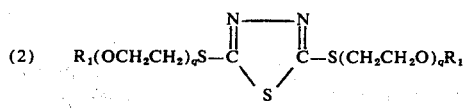

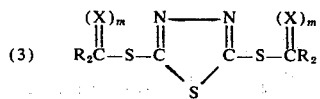

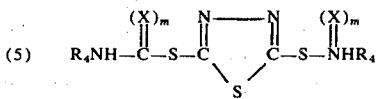

wherein:
R, $R_2$, $R_3$ and $R_4$ are $C_1$–$C_{25}$ hydrocarbyls;
$R_1$ is selected from the group consisting of a $C_1$–$C_{200}$ hydrocarbyl group and an alkenylsuccinic group;
X is oxygen or sulfur; and
m and q are zero or 1.

The invention also provides lubricant compositions containing anticorrosion or load carrying amounts of the compound described.

DESCRIPTION OF SPECIFIC EMBODIMENTS

The various products of this invention as set forth by formulas 1 to 5 in the Summary are generally prepared by reacting the appropriate organic or organic phosphorus moiety with the dimercapto thiadiazole, as follows:

FORMULA (1)

The phosphite derivatives, that is, where $m=0$ in formula (1), may be prepared by several methods known to the art. One of these involves reacting the disodium salt of 2,5-dimercapto-1,3,4-thiadiazole with about a three-fold excess of $PCl_3$ and treating the product thus obtained with the appropriate alcohol or phenol. Another method of obtaining the compounds comprises the step of reacting the disodium salt with the appropriate diorganophosphorochloridite ($(RO)_2PCl$).

The phosphates, i.e. where m is 1 are made similarly, but with $POCl_3$ or $(RO)_2P(X)Cl$.

Both types of reactions proceed with ease, and no extraordinary measures are required, only those well known to the art. In general, the reactions of the dimercapto compounds with $PCl_3$ and of the resulting product with alcohol or phenol can be carried out from about 25° to about 150°C.

The hydrocarbyl group (R) in formula (1) is an alkyl containing from 1 to 25 carbon atoms, an aryl group of from 6 carbon atoms to 14 carbon atoms, including aryls substituted with an alkyl. These include methyl, ethyl butyl, octyl octadecyl, eicosyl, pentacosyl, cresyl, ethylphenyl, butylphenyl, octylphenyl, dodecylphenyl, benzyl, phenylethyl, phenyl, naphthyl and anthryl.

FORMULA (2)

This formula embraces various compounds made by reacting related moieties with the dimercapto thiadiazole molecule. One such compound is made by reacting the disodium salt of the dimercapto compound with an organic halide such as benzyl chloride. Other compounds within this formula include those made by reacting the dimercapto compound with vinyl acetate, alkyl vinyl ether, wherein the alkyl contains from 3 to 20 carbon atoms and alkenyl-substituted succinic anhydride. One method of preparing these derivatives involves reacting one molar equivalent of the dimercapto compound with two molar equivalents of the organic halide, vinyl acetate, alkyl vinyl either or alkenylsuccinic anhydride in a solvent such as benzene. At the end of the exothermic reaction, the reaction mixture is refluxed for from 8 to 24 hours, the inorganic salts (if any) are removed and the solvent is stripped.

The organic halides (i.e. chloro, bromo, iodo, fluoro) useful in the practice of this invention include alkyl halides, wherein the alkyl has from 1 to 200 carbon atoms, as for example octyl bromide and polybutenylchloride, aryl halides (e.g. nitro-chloro benzene) alkaryl halides (e.g. nitro-chloro ethylbenzene) and aralkyl halides (e.g. benzyl chloride).

The alkenyl portions of the succinic anhydrides are derived from olefins, both mono- and polyolefins having from 2 to about 22 carbon atoms. As an example, the polybutenyl in polybutenylsuccinic anhydride is made by polymerizing butene to a molecular weight of about 200 to about 2400 and reacting it with the dimercapto compound.

The $C_1-C_{200}$ hydrocarbyl group ($R_1$) includes, in addition to those named under this point, the entities disclosed for R under Formula (1).

FORMULA (3)

Simply, the compounds of this formula are made by reacting the dimercapto compound with an organic acid halide under conditions similar to those stated for the compounds of Formula (2). The $R_2$ group has the same meaning as R which is defined above under Formula (1).

FORMULA (4)

The formula (4) compounds are made by first reacting $SO_2Cl_2$ with the disodium salt of dimercapto compound to obtain the chloride, thus:

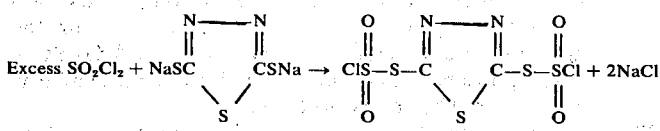

The product obtained is then reacted under known conditions with an alcohol or phenol to give the final material as defined in formula (4) hereinabove. $R_3$ has the same meaning as R, defined in the discussion of formula (1).

FORMULA (5)

The compounds hereunder are made by reacting an alkyl or aryl isocyanate with the dimercapto compound. The reaction is carried out under conditions familiar to the art. The useful isocyanates include those in which the aryl portion contains from 6 to 10 carbon atoms, and the alkyl portion contains 1 to 18 carbon atoms. Specifically, some of the reactive cynates included are phenylisocyanate and octadecylisocyanate.

Having described the invention in a general way, the following examples are offered as illustrations only and are not intended to limit the invention.

EXAMPLE 1

Phosphorus trichloride, 411g (3 moles) was charged into a reaction flask equipped with a thermometer, condenser with a drying tube attached, a mechanical stirrer and a nitrogen inlet. While stirring at room temperature, a slurry of 0.5 moles of the disodium salt of 2,5-dimercapto-1,3,4-thiadiazole in 350 ml of 1,2-dimethoxyethane was added in portions to the phosphorus trichloride.

Following the exothermic reaction, the mixture was refluxed for about 2 hours and the excess phosphorus trichloride was completely stripped under nitrogen purge.

Butyl alcohol, one mole, was then added dropwise, with stirring. Following the exothermic reaction, the mixture was refluxed for 3 hours. After cooling, the reaction mixture was treated with water and benzene. The organic extract was stripped of solvent to give the product.

EXAMPLES 2 AND 3

These products were prepared substantially in accordance with the procedure of Example 1 except that the octyl- and nonylphenyl groups, respectively, were used.

EXAMPLE 4

A reaction flask protected from moisture was charged with 0.25 mole of 2,5-dimercapto-1,3,4-thiadiazole, 500 ml of benzene and 0.6 moles of triethylamine. To the mixture was added 0.5 mole of dibutyl phosphorochloridate. Following the exothermic reaction, the mixture was stirred at 40°–50°C for 2 hours. After cooling, it was treated with water and benzene. The organic extract was stripped of solvent to give the product. The product contained 17.4% sulfur (calculated — 17.9%).

EXAMPLE 5

To a slurry of 0.25 mole of the disodium salt of 2,5-dimercapto-1,3,4-thiadiazole in 200 ml of 1,2-dimethoxyethane was added dropwise, 0.5 mole of dioctylphosphorochloridate. After the addition was completed and the exothermic reaction had subsided, the reaction mixture was refluxed for 2 hours, was cooled and was then treated with benzene and water. The organic layer was stripped under vacuum to give the product. The product contained 3.6% N (calculated — 3.7%)

EXAMPLES 6–8

These were made substantially in accordance with the procedure of Example 4 using the appropriate reactants.

EXAMPLE 9

Made substantially in accordance with Example 5, except benzyl chloride was used instead of the diorganophosphorochloridate.

EXAMPLE 10

Made substantially in accordance with Example 5, except benzoyl chloride was used instead of diorganophosphorochloridate.

EXAMPLES 11–12

These examples are prepared substantially in accordance with the procedure of Example 10.

EXAMPLE 13

A slurry of 0.2 mole of the disodium salt of 2,5-dimercapto-1,3,4,-thiadiazole in carbon tetrachloride was added in portions to an excess (about three-fold) of sulfuryl chloride. After the exothermic reaction moderated, the mixture was stirred for an additional 8 hours, and was heated briefly at 40°–50°C. The excess sulfuryl chloride was stripped under vacuum. To a solution of the residue in 1,2-dimethoxyethane was added 0.38 mole of octylalcohol and the mixture was refluxed for 5 hours. It was then reacted with benzene, water and butanol. The organic extract was stripped under vacuum to give a solid product.

EXAMPLE 14

The product was prepared substantially as set forth in Example 13.

EXAMPLE 15

To 1 mole of butylvinylether in a reaction flask was added, dropwise, a mixture of 0.3 mole of 2,5-dimercapto-1,3,4-thiadiazole, 0.04 mole of tributylamine and 100 ml of 1,2-dimethoxyethane. After the addition, the reaction mixture was refluxed overnight. It was then treated with benzene and water. The organic extract was stripped under vacuum to give the product.

EXAMPLE 16

The product was made substantially in accordance with Example 15, substituting vinyl acetate for butylvinylether.

EXAMPLE 17

Polybutenylsuccinic anhydride (0.1 mole), 0.05 mole of 2,5-dimercapto-1,3,4-thiadiazole and 100 ml of 1,2-dimethoxyethane were refluxed for 24 hours. The solvent was stripped under vacuum to give the product. The product was also made using 0.05 mole of the disodium salt of the dimercapto thiadiazole. When the sodium salt was used, the reaction mixture, after refluxing for 24 hours, was trated with diluted HCl and benzene. The organic extract was stripped under vacuum to give the product.

EXAMPLES 18–19

These were prepared essentially as outlined in Example 17 except that dodecenylsuccinic anhydride and octenylsuccinic anhydride, respectively, were used.

EXAMPLE 20

To a slurry of 0.4 mole of the disodium salt of 2,5-dimercapto-1,3,4-thiadiazole in 350 ml of 1,2-dimethoxyethane was added, dropwise, 0.8 mole of phenylisocyanate. Following the initial exothermic reaction, the mixture was refluxed for about 6 hours, cooled and treated with diluted HCl. It was then extracted with a benzene-ether mixture. The organic portion was stripped under vacuum to give the product.

EVALUATION OF PRODUCTS

Shell Four-Ball Test

The products were evaluated in the Shell Four-Ball Wear Test. Four ½ inch 52100 steel balls were placed under 60 Kg pressure for 30 minutes at the temperatures and speeds shown in Table 1. The oil used was a mixture of 80 parts of solvent refined Mid-Continent paraffinic 150/160 bright mineral oil and 20 parts of furfural refined Mid-Continent 200/210 neutral mineral oil.

Copper Corrosion Test

A standard copper strip, as defined in ASTM D-130, was polished and placed in a test tube. Test oil containing the additive was poured into the tube so that the strip was covered, and the tube was immersed for 3 hours in a water bath at a temperature of 250°F. At the end of the 3 hours, the strip was removed, wiped dry and checked for corrosion by comparing it with standard ASTM copper strips. The oil used was a base stock comprising a mixture of (1) furfural refined Mid-Continent 200/210 neutral mineral oil and (2) solvent refined 130 second bright mineral oil containing a sulfurized olefin antiwear agent. The results are shown in Table II.

TABLE I

| Example | Additive | Conc. Wt. % | Temp. °F. | Scar Diameter, mm SPEED (RPM) | | | |
|---|---|---|---|---|---|---|---|
| | | | | 500 | 1000 | 1500 | 2000 |
| | Base Stock | 100 | Room | 0.50 | 0.60 | 0.88 | 2.34 |
| | | | 200 | 0.060 | 1.06 | 0.86 | 2.23 |
| | | | 390 | 1.0 | 1.31 | 2.08 | — |
| 1 | $(C_4H_9O)_2P-S-C\underset{S}{\overset{N-N}{\diagdown\diagup}}C-S-P(OC_4H_9)_2$ | 1 | 200 | 0.55 | 0.50 | 0.50 | 0.70 |
| | | | 390 | 0.55 | 0.60 | 0.75 | 0.70 |
| 2 | $(C_8H_{17}O)_2P-S-C\underset{S}{\overset{N-N}{\diagdown\diagup}}C-S-P(OC_8H_{17})_2$ | 1 | 200 | 0.40 | 0.50 | 0.50 | 0.50 |
| | | | 390 | 0.50 | 0.80 | 1.0 | 1.0 |
| 3 | $(C_9H_{19}\text{-}\langle O\rangle\text{-}O)_2P-S-C\underset{S}{\overset{N-N}{\diagdown\diagup}}C-S-P-(O\text{-}\langle O\rangle\text{-}C_9H_{19})_2$ | 1 | Room | 0.40 | 0.40 | 0.60 | 0.90 |
| | | | 200 | 0.50 | 0.55 | 0.80 | 0.80 |
| | | | 390 | 0.50 | 0.60 | 0.65 | 1.25 |

TABLE I-continued

| Example | Additive | Conc. Wt. % | Temp. °F. | Scar Diameter, mm SPEED (RPM) | | | |
|---|---|---|---|---|---|---|---|
| | | | | 500 | 1000 | 1500 | 2000 |
| 4 | (C$_4$H$_9$O)$_2$P(O)—S—C(=N—N=)C—S—P(O)(OC$_4$H$_9$)$_2$ (S ring) | 1 | Room | 0.40 | 0.65 | 0.65 | 0.76 |
| | | | 200 | 0.60 | 0.70 | 0.76 | 0.75 |
| | | | 390 | 0.60 | 1.0 | 1.10 | 0.80 |
| 5 | (C$_8$H$_{17}$O)$_2$P(O)—S—C(=N—N=)C—S—P(O)(OC$_8$H$_{17}$)$_2$ (S ring) | 1 | Room | 0.45 | 0.60 | 0.80 | 0.90 |
| | | | 200 | 0.50 | 0.80 | 1.0 | 1.05 |
| | | | 390 | 0.80 | 1.0 | 1.0 | 1.15 |
| 6 | (CH$_3$O)$_2$P(O)—S—C(=N—N=)C—S—P(O)(OCH$_3$)$_2$ (S ring) | 1 | 200 | 0.80 | 0.80 | 1.30 | 1.50 |
| | | | 390 | 0.90 | 1.10 | 1.45 | 1.30 |
| 7 | [(C$_9$H$_{19}$—C$_6$H$_4$—O)$_2$P(O)—S—C(=N—N=)C—S—P(O)(O—C$_6$H$_4$—C$_9$H$_{19}$)$_2$] (S ring) | 1 | 200 | 0.50 | 0.50 | 0.75 | 0.95 |
| | | | 390 | 0.50 | 0.70 | 0.85 | — |
| 8 | (C$_6$H$_5$O)$_2$P(O)—S—C(=N—N=)C—S—P(O)(OC$_6$H$_5$)$_2$ (S ring) | 1 | 200 | 0.45 | 0.60 | 0.80 | 1.50 |
| | | | 390 | 0.85 | 1.0 | 1.90 | — |
| 9 | C$_6$H$_5$—CH$_2$S—C(=N—N=)C—SCH$_2$—C$_6$H$_5$ (S ring) | 1 | 200 | 0.50 | 0.60 | 0.70 | 0.85 |
| | | | 390 | 0.90 | 0.70 | 1.10 | 1.80 |
| 10 | C$_6$H$_5$—C(O)—S—C(=N—N=)C—S—C(O)—C$_6$H$_5$ (S ring) | 0.25 | 200 | 0.50 | 0.60 | 1.65 | — |
| | | | 390 | 0.90 | 1.0 | 1.60 | — |
| 11 | (CH$_3$)$_3$C—C(O)—S—C(=N—N=)C—S—C(O)—C(CH$_3$)$_3$ (S ring) | 1 | Room | 0.46 | 0.80 | 0.90 | 1.40 |
| | | | 200 | 0.70 | 1.00 | 1.30 | 1.45 |
| | | | 390 | 1.10 | 1.43 | — | — |
| 12 | CH$_3$(CH$_2$)$_{16}$C(O)—S—C(=N—N=)C—S—C(O)(CH$_2$)$_{16}$CH$_3$ (S ring) | 1 | Room | 0.50 | 0.60 | 0.85 | 1.20 |
| | | | 200 | 0.70 | 0.80 | 1.05 | 1.20 |
| | | | 390 | 1.0 | 1.45 | — | — |
| 13 | C$_8$H$_{17}$OS(O)$_2$—S—C(=N—N=)C—S—S(O)$_2$O—C$_8$H$_{17}$ (S ring) | 1 | 200 | 0.50 | 0.50 | 0.65 | 0.75 |
| | | | 390 | 0.50 | 0.80 | 0.90 | 1.10 |
| 14 | C$_{12}$H$_{25}$OS(O)$_2$—S—C(=N—N=)C—S—S(O)$_2$O—C$_{12}$H$_{25}$ (S ring) | 1 | 200 | 0.50 | 0.65 | 085 | 0.90 |
| | | | 390 | 0.95 | 0.85 | 0.90 | 1.95 |
| 15 | CH$_3$C(O)—OCH$_2$CH$_2$S—C(=N—N=)C—SCH$_2$CH$_2$OC(O)CH$_3$ (S ring) | 1 | 200 | 0.60 | 1.0 | 1.15 | 1.15 |
| | | | 390 | 1.0 | 1.25 | 1.40 | 1.25 |
| 16 | C$_4$H$_9$OCH$_2$CH$_2$S—C(=N—N=)C—SCH$_2$CH$_2$OC$_4$H$_9$ (S ring) | 1 | 200 | 0.50 | 0.80 | 1.30 | — |
| | | | 390 | 1.0 | 1.35 | 1.45 | 1.55 |
| 17 | *PB—CH—C(O)—S—C(=N—N=)C—S—C(O)—CH—PB* (S ring) | 1 | 200 | 0.50 | 0.70 | 0.90 | 0.95 |
| | | | 390 | 0.60 | 1.40 | — | — |
| 18 | C$_{12}$H$_{23}$—CH(CH$_2$—COOH)—C(O)—S—C(=N—N=)C—S—C(O)—CH(CH$_2$—COOH)—C$_{12}$H$_{23}$ (S ring) | | 200 | 0.50 | 1.95 | — | — |
| | | | 390 | 1.0 | 1.50 | — | — |

TABLE I-continued

| Example | Additive | Conc. Wt. % | Temp. °F. | Scar Diameter, mm SPEED (RPM) | | | |
|---|---|---|---|---|---|---|---|
| | | | | 500 | 1000 | 1500 | 2000 |
| 19 | $C_8H_{15}-CH-\overset{O}{\overset{\|}{C}}-S-\overset{N-N}{\underset{S}{\overset{\|}{C}}}\overset{O}{\underset{\|}{C}}-S-\overset{O}{\overset{\|}{C}}-CH-C_8H_{15}$ with $CH_2-COOH$ groups | 1 | 200 390 | 0.50 0.70 | 0.65 0.85 | 0.95 1.70 | 1.0 — |
| 20 | $C_6H_5NH\overset{O}{\overset{\|}{C}}S-\overset{N-N}{\underset{S}{\overset{\|}{C}}}\overset{O}{\underset{\|}{C}}-S\overset{O}{\overset{\|}{C}}HNC_6H_5$ | 1 | 200 390 | 0.60 0.80 | 0.90 — | 1.10 — | 1.30 — |

* From Polybutenyl where the polybutenyl has a number average molecular weight of 2300

TABLE II

| | Copper Corrosion Test | |
|---|---|---|
| Example | Additive Conc. | Result |
| Base Stock | — | 3B |
| 5 | 0.5% | 2B |
| 6 | 0.5% | 1B |
| 7 | 0.5% | 2A |
| 8 | 0.5% | 2A |
| 9 | 0.5% | 3A |
| 16 | 0.5% | 3A |
| 17 | 0.5% | 2E |
| 19 | 0.5% | 2B |
| 20 | 0.5% | 1B |

I claim:

1. A lubricant composition comprising a major proportion of a lubricant and an antiwear or corrosion inhibiting amount of a compound of the formula:

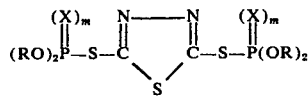

wherein:
R is $C_1-C_{25}$ hydrocarbyl;
X is oxygen or sulfur; and
m is zero or 1.

2. The composition of claim 1 having therein a compound according to formula 1 wherein R is butyl and m is zero.

3. The composition of claim 1 having therein a compound according to formula 1, wherein R is butyl, X is oxygen and m is 1.

4. The composition of claim 1 having therein a compound according to formula 1, wherein R is octyl and m is zero.

5. The composition of claim 1 having therein a compound according to formula 1, wherein R is octyl, X is oxygen and m is 1.

6. The composition of claim 1 having therein a compound according to formula 1, wherein R is nonylphenyl and m is zero.

7. The composition of claim 1 having therein a compound according to formula 1, wherein R is nonylphenyl, X is oxygen and m is 1.

* * * * *